(12) United States Patent
Griffin et al.

(10) Patent No.: US 11,649,423 B2
(45) Date of Patent: May 16, 2023

(54) CELL HARVESTING APPARATUS

(71) Applicant: Global Life Sciences Solutions USA LLC, Marlborough, MA (US)

(72) Inventors: Weston Blaine Griffin, Niskayuna, NY (US); Austin Lines, Merrimack, NH (US); Dan Harris, Merrimack, NH (US); David Schuelke, Hudson, WI (US); Krystal Burger, Hudson, WI (US)

(73) Assignee: Global Life Sciences Solutions USA LLC, Marlborough, MA (US)

( * ) Notice: Subject to any disclaimer, the term of this patent is extended or adjusted under 35 U.S.C. 154(b) by 653 days.

(21) Appl. No.: 16/065,413

(22) PCT Filed: Dec. 22, 2016

(86) PCT No.: PCT/EP2016/082382
§ 371 (c)(1),
(2) Date: Jun. 22, 2018

(87) PCT Pub. No.: WO2017/109072
PCT Pub. Date: Jun. 29, 2017

(65) Prior Publication Data
US 2019/0017005 A1 Jan. 17, 2019

Related U.S. Application Data

(60) Provisional application No. 62/270,917, filed on Dec. 22, 2015.

(51) Int. Cl.
*B01L 3/00* (2006.01)
*C12M 1/00* (2006.01)
(Continued)

(52) U.S. Cl.
CPC ............ *C12M 1/26* (2013.01); *A61M 1/0281* (2013.01); *B01L 3/50273* (2013.01);
(Continued)

(58) Field of Classification Search
CPC ............... B01L 3/50273; C12M 47/02; C12M 33/14; C12M 1/26; A61M 1/0281; A61M 2205/125; A61M 2205/123
See application file for complete search history.

(56) References Cited

U.S. PATENT DOCUMENTS 5,036,001 A 7/1991 Gork et al.
8,177,974 B2 5/2012 Hunt et al.
(Continued)

FOREIGN PATENT DOCUMENTS

JP 2012152124 A 8/2012
WO 03087292 A2 10/2003
(Continued)

OTHER PUBLICATIONS

Notification of Transmittal of the International Search Report and the Written Opinion of the International Searching Authority, or the Declaration from International Appl. No. PCT/EP2016/082382, dated Apr. 12, 2017.
Chinese Office Action for CN Application No. 201680082329.4 dated Jul. 2, 2021 (19 pages).
Chinese Office Action for CN Application No. 201680082332.6 dated Apr. 12, 2021 (12 pages with English translation).
(Continued)

*Primary Examiner* — Liban M Hassan
(74) *Attorney, Agent, or Firm* — Eversheds Sutherland (US) LLP

(57) ABSTRACT

Disclosed herein is a cell harvesting instrument suitable for concentrating cells from a source suspension of cells and/or washing said cells, the instrument comprising: a housing for accommodating mechanical elements including at least one
(Continued)

fluid pump, at least one valve; and a processing kit removably insertable into the housing, said kit including a generally flat frame having or supporting plural sealed fluid paths arranged in a generally flat plane and such that fluids in the paths do not contact said mechanical elements, wherein at least portions of the fluid paths comprise flexible tubes, the outer surfaces of which are manipulateable by the or each fluid pump, to provide fluid flow in one or more of the paths and/or by the or each valve to restrict fluid flow in one or more of the paths. In an embodiment, the kit comprises also a fluid processing reservoir and a filter suitable for separating cells from fluid in said paths. A transfer mechanism for moving and weighing the fluid processing reservoir is disclosed also.

6 Claims, 18 Drawing Sheets

(51) Int. Cl.
  *C12M 1/26* (2006.01)
  *A61M 1/02* (2006.01)
(52) U.S. Cl.
  CPC ............ *C12M 33/14* (2013.01); *C12M 47/02* (2013.01); *A61M 2205/123* (2013.01); *A61M 2205/125* (2013.01)

(56) References Cited

U.S. PATENT DOCUMENTS

| | | | |
|---|---|---|---|
| 8,492,140 B2 * | 7/2013 | Smith | .................... C12M 25/14 435/289.1 |
| 8,597,229 B2 | 12/2013 | Pan | |
| 10,982,183 B2 | 4/2021 | Harris | |
| 2002/0083998 A1 | 7/2002 | Overbeck et al. | |
| 2011/0085746 A1 | 4/2011 | Wong et al. | |
| 2013/0029411 A1 | 1/2013 | Roy et al. | |
| 2015/0160250 A1 | 6/2015 | Bucher et al. | |

FOREIGN PATENT DOCUMENTS

| | | |
|---|---|---|
| WO | 2006119622 A1 | 11/2006 |
| WO | 2011080072 A1 | 7/2011 |
| WO | 2017109072 A1 | 6/2017 |

OTHER PUBLICATIONS

Chinese Office Action for CN Application No. 201680082332.6 dated Jan. 6, 2022 (10 pages).

Chinese Office Action for CN Application No. 201680082332.6 dated Apr. 9, 2021 (12 pages with English translation).

* cited by examiner

CELL HARVESTING APPARATUS

This invention relates to cell harvesting apparatus, to the improved functioning of such apparatus, and to improvements in the components thereof.

BACKGROUND

Effective harvesting of cells from various sources is required for different therapeutic applications, such as cell therapy, or tissue engineering. The examples of therapeutic applications include but are not limited to autologous or allogeneic transplantation of stem cells, transplantation of matured functional cells, T cells, modified human cells including T cells, or xenotransplantation of non-human cells. The applications facilitate healing of the damaged tissue or an organ, by regenerating cells to improve the condition of a diseased state.

For translational research, which facilitates the development and implementation of scientific discoveries to prevent, diagnose, and treat disease using state-of-the-art technologies, a range of potential cell types require isolation prior to modification, activation, and/or expansion. To meet this translational market need, the cells are first required to be concentrated and washed to remove any impurities. For preserved cell applications, where previously separated mononucleated cells (MNC) are stored in cryogenic temperatures after suspension in media containing preservatives such as dimethylsulfoxide (DMSO), the cells need to be washed, typically through a dilution process, several times to minimize the preservative's concentration before re-concentrating and re-suspending the cells for use. Therefore, the processing of cryo-preserved cells is necessary before use in any application, specifically for therapeutic application or research purposes.

For both of the examples, a suspension of such cells should be processed to concentrate and should be washed extensively to ensure high quality-herein, such concentration optionally including one or more wash cycles is referred to as cell harvesting. Although various methods and systems for harvesting cells are known in the art, the quality and quantity output of these systems are insufficient for therapeutic application. Therefore, systems and methods for harvesting cells under aseptic conditions not necessarily in large scale processing facilities, but with reduced infrastructure requirements and robust operational efficiency, are highly desirable. In additional, equipment which is simple to operate and to maintain is desirable also.

BRIEF DESCRIPTION

Methods and devices for harvesting cells are described in patent application US2013/0029411, the contents of which are incorporated herein by reference, and result in high quality cell samples, which are devoid of significant residual impurities or preservatives. These methods and devices resolve some of the problems associated with the cells used for translational applications or cells recovered from cryogenic preserved cells.

An example of method of harvesting cells from a fluidic material in a processing loop as shown in US2013/0029411 comprises, a processing chamber and a filtering device wherein the fluidic material has a volume and the processing chamber has an overall capacity, comprises circulating the fluidic material through the processing loop and balancing an influx of the fluidic material into the processing chamber with a permeate flux of the filtering device to maintain the volume of the fluidic material in the processing chamber at a constant value, concentrating the cells by increasing the permeate flux of the filtering device relative to the influx of the fluidic material into the processing chamber; and collecting the concentrated cells in a collection chamber. Other examples of the method of harvesting cells from a fluidic material in a processing loop are shown in US2013/0029411.

In addition, embodiments of the cell harvesting devices are shown US2013/0029411 comprising, for example, a processing loop comprising a processing chamber and a filtering device; a network of input and output lines operatively coupled to one or more of a source chamber, buffer chamber, waste chamber and collection chamber, and a controller that controls a mass of the processing chamber at a desired value based on an influx and a permeate flux of the processing loop.

The inventors have devised improvements to the methods and devices disclosed in US2013/0029411, which have resulted in improved performance and reliability, as well as reduced costs in the consumable parts of the improvements. Embodiments of the invention address the shortcomings of known cell harvesting equipment. The invention is set out in the independent claims herein, with preferred features defined in dependent claims.

DRAWINGS

These and other features, aspects, and advantages will become better understood when the following detailed description is read with reference to the accompanying drawings in which like characters represent like parts throughout the drawings, wherein.

DETAILED DESCRIPTION

To more clearly and concisely describe and point out the subject matter of the claimed invention, the following definitions are provided for specific terms, which are used in the following description and the appended claims. Throughout the specification, use of specific terms should be considered as non-limiting examples.

Figure 1:
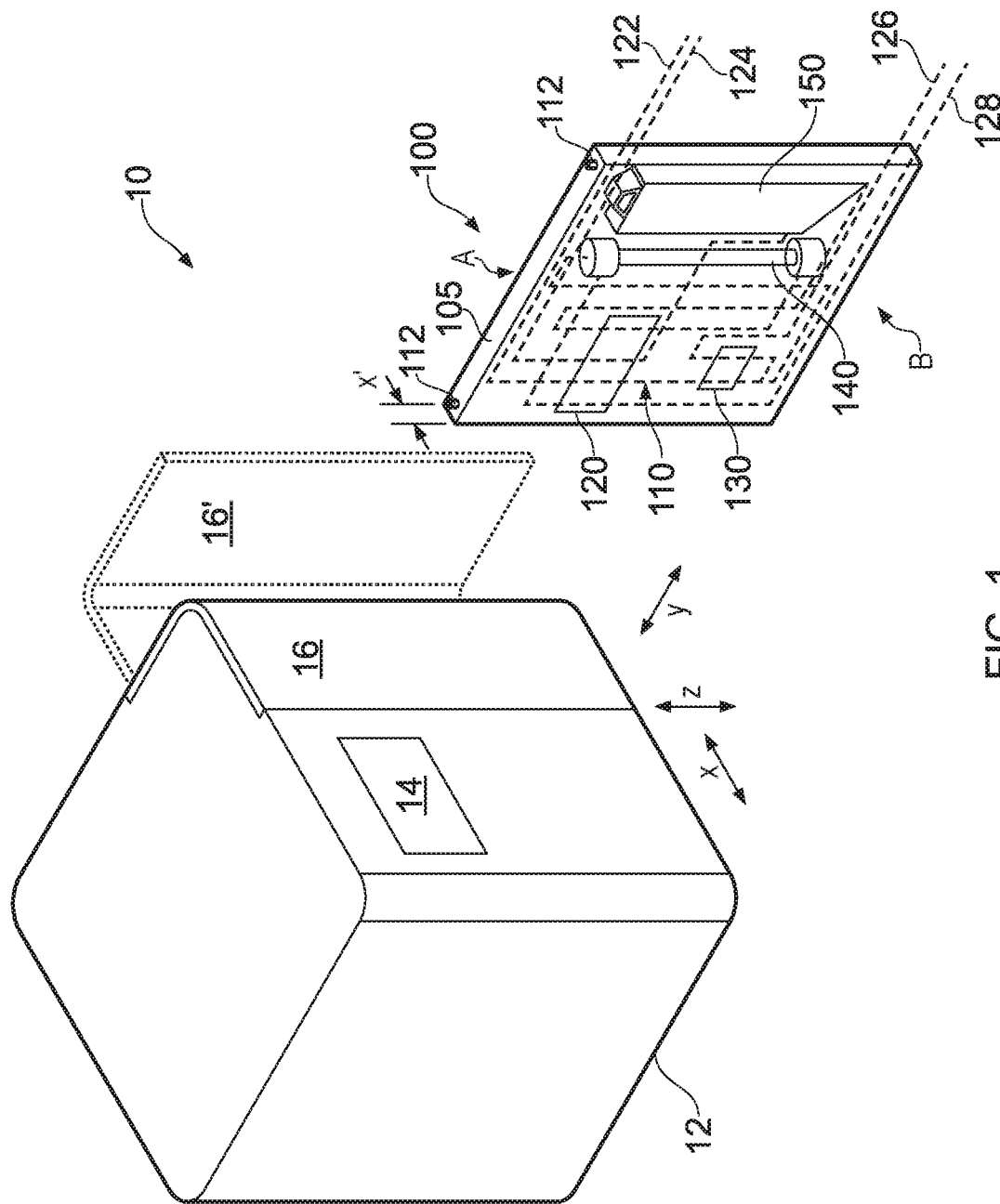
FIG. 1 shows a cell harvesting instrument together with its disposable processing kit.

Referring to FIG. 1 there is shown a cell harvesting instrument 10, which in use functions to take in liquids which include suspended cells or similar microbiological material, for the purpose of largely separating the cells from the liquid or reducing the liquid content of the suspension. The instrument can function to wash the cells etc. one or more times to rid the separated cells of unwanted material. A preferred functioning regime can be found in US2013/0029411.

The instrument 10 comprises a housing 12 which has a touch screen 14 and a door 16, shown closed and, in chain dotted lines, shown in an open position 16'. The door 16 allows the insertion and removal of a disposable processing kit 100. The kit 100 is generally flat with a peripheral support frame 105 of thickness x' in the x direction of around 30-40 mm. In other words, fluid paths 110 within the frame, and additional components of the kit described below, lie substantially in a generally flat, single, plane. The liquid paths 110, shown in chain dotted lines have, in this case, four inlets/outlets 122, 124, 126, and 128. The fluid paths 110 are mostly constructed from medical grade tubing, for example PVC tubing. Other than those inlets/outlets 122-128, the fluid paths 110 are functional closed circuits, which are sealed, other than at vents which have filters containing sub-micron pore size filters to allow gases to escape, but to prevent ingress of contamination. In particular, mechanical parts contained within the housing 12, do not contact any fluids in the paths, thereby maintaining sterility of the paths in use. The frame 105 also includes through-apertures 120 and 130 which run from one side of the frame 105 to the other, providing regions where the tubes of the fluid paths which pass across the apertures can be manipulated from both sides of the frame by said mechanical parts. Where the fluid paths cross the apertures, these tubes need to be flexible, and so these tubes are preferably formed from silicon tubing.

The kit 100 further includes a tangential flow filter 140, and a detachable process reservoir 150, in this case in the form of a moulded plastics container. The processing kit 100 is inserted into and removed from the housing 12 in the direction of arrow y.

Figure 2:
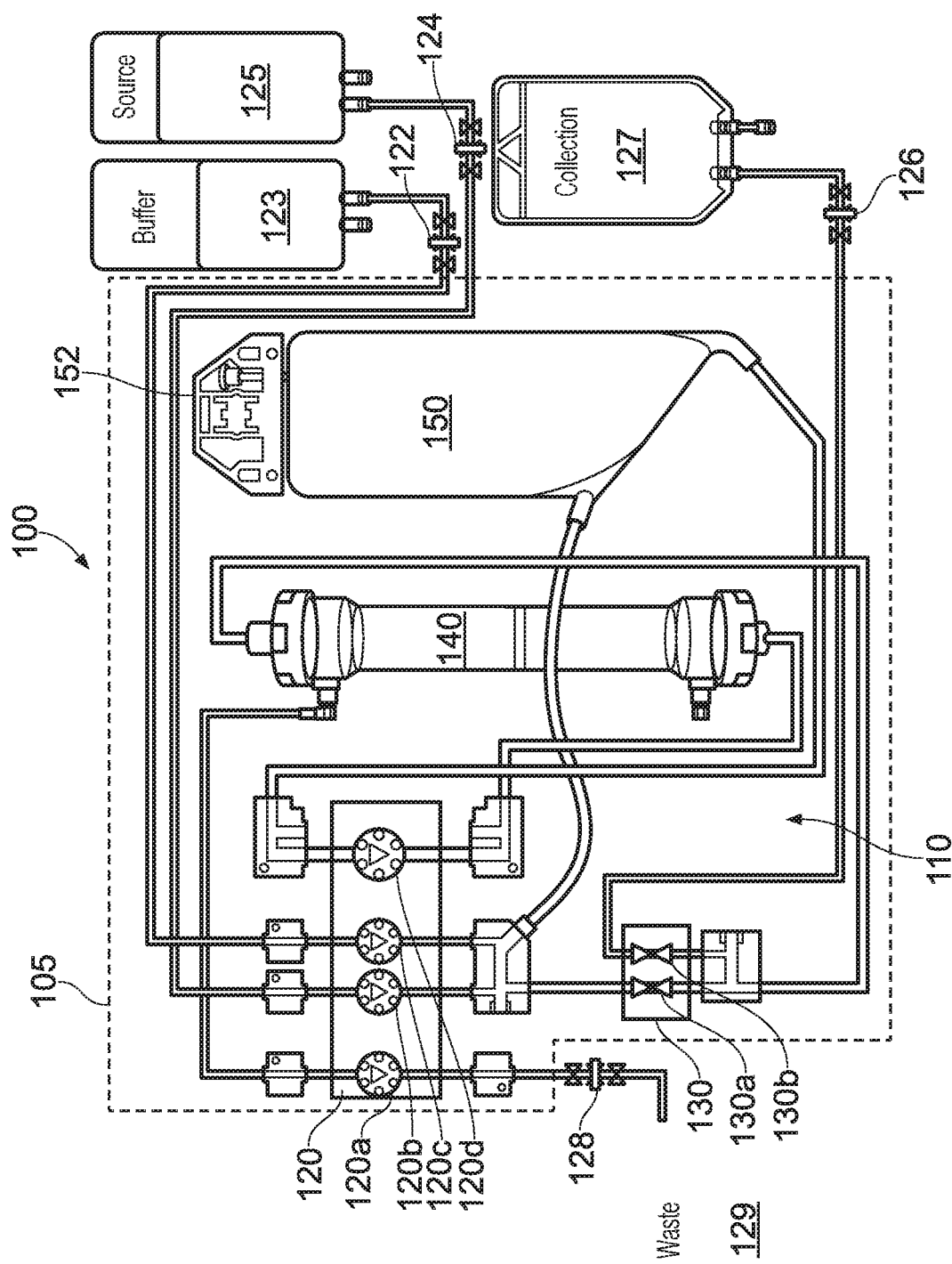
FIG. 2 shows a schematic representation of the disposable processing kit shown in FIG. 1.

FIG. 2 is a side view of the processing kit 100 and shows the layout of the fluid paths 110 within the support frame 105, and its external connections which in practice are made externally of the housing 12 when the kit 100 is inserted into the housing 12 in use. The kit 100 once inserted, is connected to a buffer/wash liquid supply 123, to a source of suspended cells or similar biological material 125, to a waste collection 129 and to a harvesting collection chamber 127, each by means of a respective sterile connector 122, 124, 128 and 126. In the alternative, any of the buffer supply 123, source 125, waste collection 129, and harvesting collection chamber 127 can be pre-connected to the fluid paths 110. In practice, extended respective fluid connection tubing is coiled close to the frame 105 initially, terminating in said buffer supply 123, source 125, waste collection 129, and/or harvesting collection chamber 127, and the extended tubing is uncoiled to be fed outside of the housing 12 once the kit 100 is inserted into the housing. The through aperture 120 allows a pumping action to be exerted on fluids within the flexible tubular paths 120a, 120b, 120c and 120d which cross the aperture. Likewise, the through aperture 130 allows the tubular paths 130a and 130b that cross that aperture to be pinched to provide a valve action. The processing reservoir 150 acts as fluid holding chamber and is part of the recirculating loop, through which the cell-containing fluid actively recirculates during most of the concentration and washing process performed by the instrument 10. It is important to determine the total volume/mass of fluids in the whole processing loop, which includes the fluid paths 110, the filter 140 and the processing reservoir 150. That total will vary in use because, for example, the amount of waste fluid taken away and the amount of buffer added will alter the total volume. However, since all components except the processing reservoir 150 have a fixed working volume, the variable mass in the processing reservoir 150 is all that needs to be measured to determine the total processing loop volume/mass. Thus, the reservoir 150 includes a hanger 152 which allows its weight to be measured and thereby the total fluid volume/mass can be determined.

Figure 3:
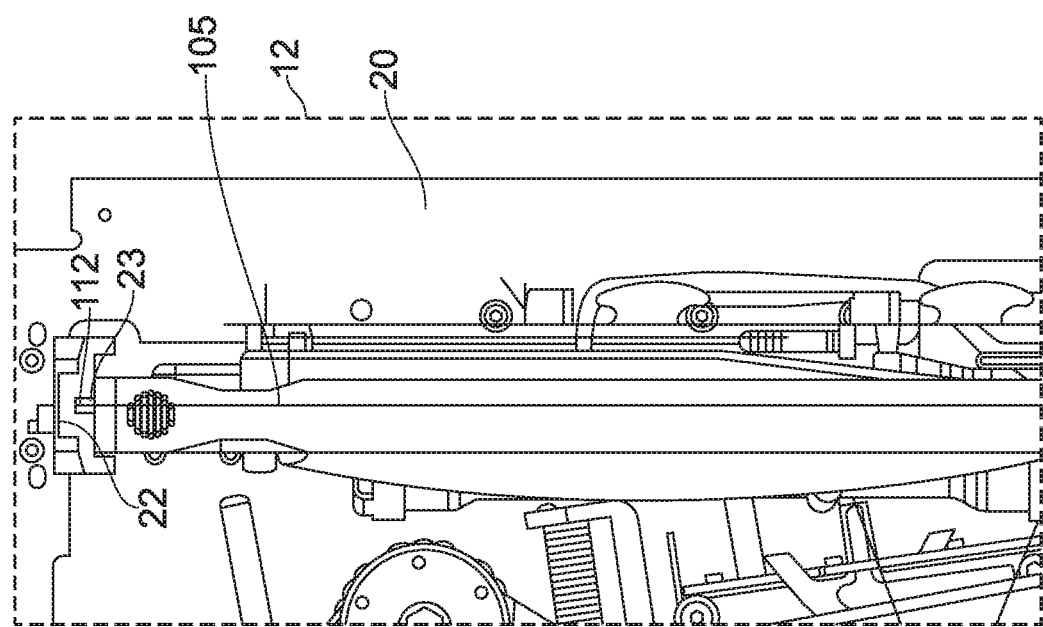
FIG. 3 shows the processing kit in place in the instrument.

FIG. 3 shows a part of the frame 105 inserted into the housing 12. In this instance the frame includes guiding formations for example I the ofrm of pegs, or ribs 112 top and bottom which locate slideably in an open ended groove 23 formed in a top guide rail 22 supported by a rigid device frame 20 within the housing 12, to slideably support and locate the kit 100.

Figure 4:
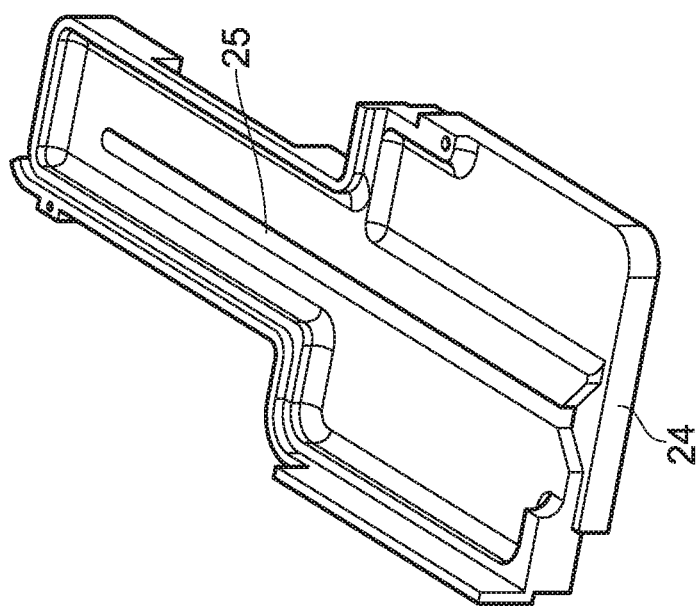
FIG. 4 shows a receiving rail mountable in the housing of the instrument of FIG. 1 for guiding the processing kit into place in the housing.

In FIG. 4 a bottom guide rail 24 is shown which also includes a groove 25 to accept pegs or a rib (not shown) on the bottom of the frame 105. The processing kit 100 is loaded into the housing 12. The bottom guide rail 24 and a top rail (22 FIG. 5), both have grooves that interface with respective pegs or ribs on the processing kit. The lower peg or rib and groove are wider than the top for two reasons: a) to make it obvious to the user which end is the top and to prevent incorrect insertion of frame 105, and b) to make it easier to clean the lower rail in the event of a processing kit leak. To aid cleanup, the bottom guide rail 24 has large radii and is dish shaped to catch any leakage. An adjustable roller detent feature (not shown) provides user tactile feedback to alert the user to stop pushing the processing kit into the housing.

Figure 5:
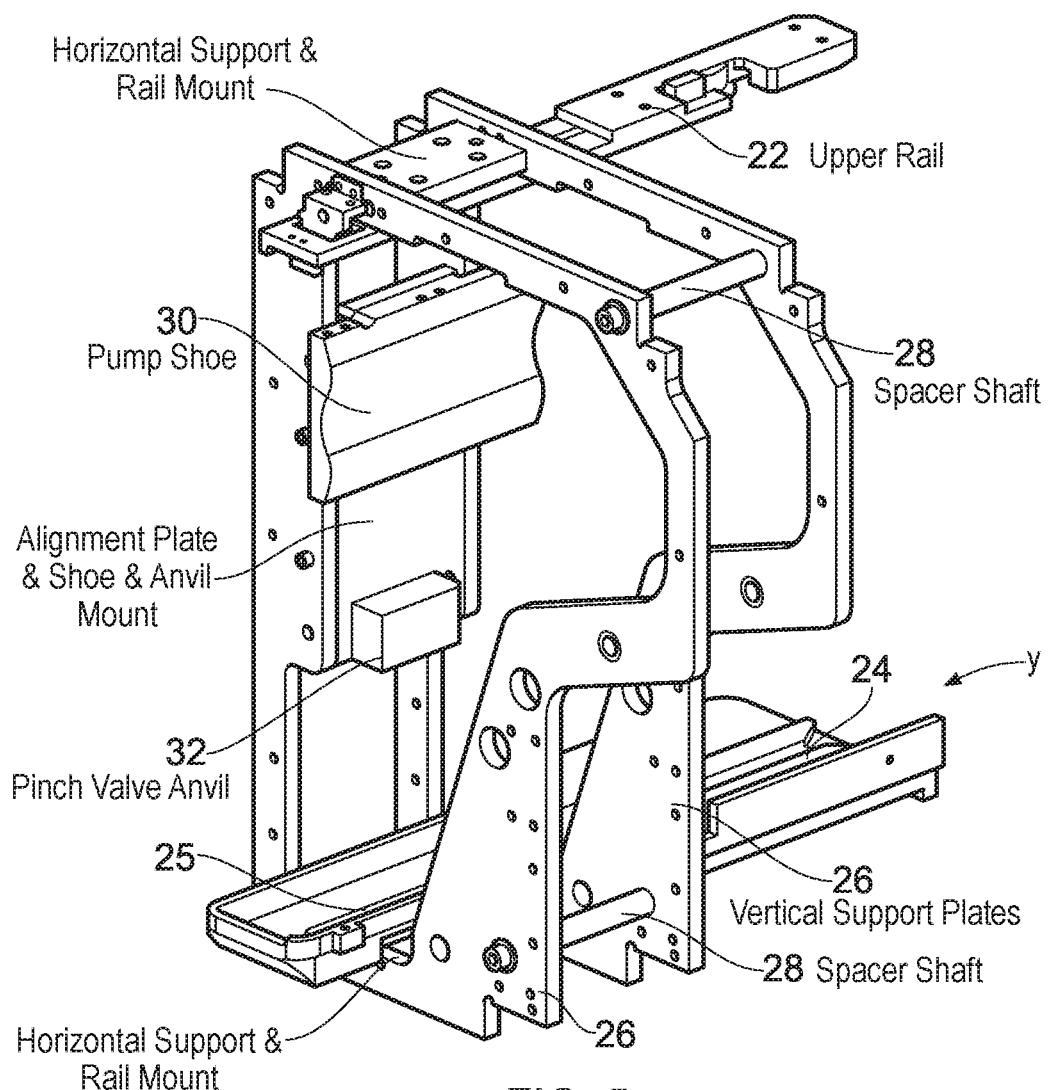
FIG. 5 shows a processing kit receiving frame which is housed within the housing of the instrument shown in FIG. 1.

FIG. 5 shows the device frame 20 in more detail, with the housing 12 removed for clarity. The direction of insertion of the kit 100 is shown by arrow, so the device frame 20 is viewed in this illustration from the rear of the housing 12 shown in FIG. 1. The device frame 20 comprises two plates 26 held in spaced relation by spacer fixings 28. The top and bottom guide rails 22 and 24 run in parallel each mounted to both of the two spaced plates 26. Also mounted to the plates are a shoe 30 for reacting the forces of a peristaltic pump rotor (described in more detail below) and an anvil to react forces exerted by a pinch valve (described in more detail below). The shoe 30 and anvil 32, in use align with the through apertures 120 and 130 respectively.

Figure 6:
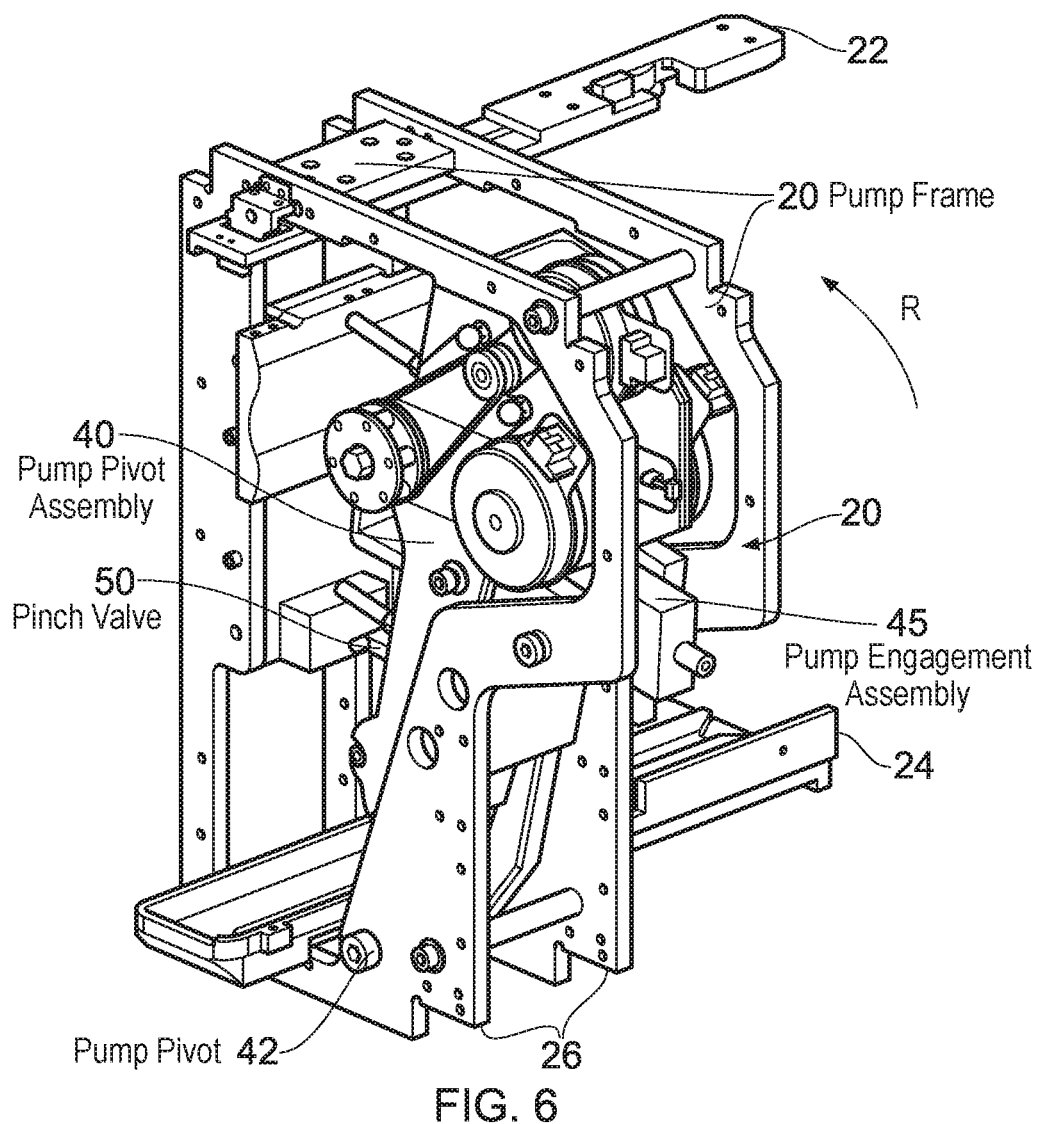
FIGS. 6 to 10 show details of a peristaltic pump mountable in the frame shown in FIG. 5

FIG. 6 shows the device frame 20, and pivotably mounted on the frame via a pivot 42, a pump assembly 40. The pump assembly in use, with the processing kit inserted into the housing 12 between guide rails 22 and 24, is pivoted in the direction of arrow R about pump pivot 42, relative to the stationary frame 20, to interact with the flexible tubes 120a,b,c and d as well as the flexible tubes 130a and b, using the shoe 30 and anvil 32 as reaction faces. Additional alignment is effected by guide pins 48 rigidly mounted to the assembly 40. The pump assembly 40 interfaces with a processing kit 100 to selectively pump fluid through the fluid paths 110 with, in this instance, a peristaltic action. The assembly 40 includes a 3 state pinch valve to direct the flow appropriately by the use of cams which compress and close the cooperating flexible tubes. The pump and valve, each described in more detail below, are supported on the frame 20 such that operational forces are isolated from the surrounding housing. Disengagement of the pump and valve is effected by pivoting in a direction opposite to arrow R, prior to removal of a used processing kit 100.

Figure 7:
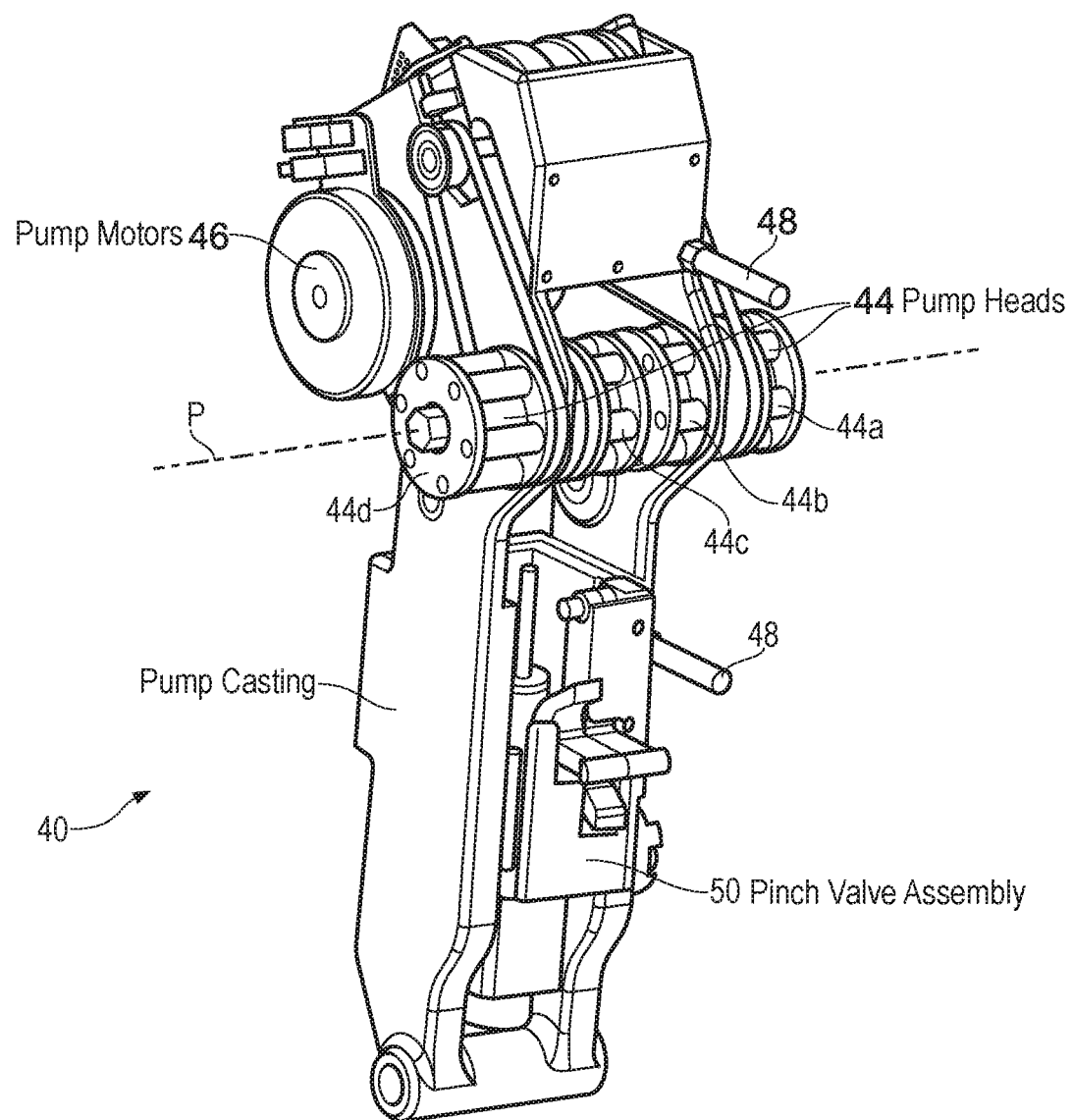

FIG. 7 shows the pump assembly in more detail, removed from the frame 20, and viewed in the direction of arrow A in FIG. 6. In this view, four pump heads 44a, 44b, 44c and 44d are visible, which interact with the flexible tubes 120a, b,c and d respectively. The heads are each formed from sets of rollers each mounted for rotation about a roller pin, and each pin mounted for rotation about a pump axis P, thereby forming the head of a peristaltic pump. The four heads share the same pump axis P but can be rotated independently by four different servo type motors 46 acting on drive belts to provide controlled and reversible fluid pressure differentials in the fluid paths 120a to d. The pivoting of the whole pump assembly 40 into a pumping position is effected by an electrical actuator 44 mounted to the assembly 40 and reacting against the frame 20. During the movement of the pump assembly into an operative position, guide pins 48 cooperate with complementary formations on the processing kit support frame 105, so that the kit and pump heads are aligned more accurately than relying only on the guide rails 22 and 24. The pump heads have six generally evenly spaced rotors, which when engaged against a shoe 30 of approximately 70° arc provides at least one roller always in contact with the shoe, thereby preventing reverse fluid flow and fluid flow if the pump is not turning.

Figure 8:
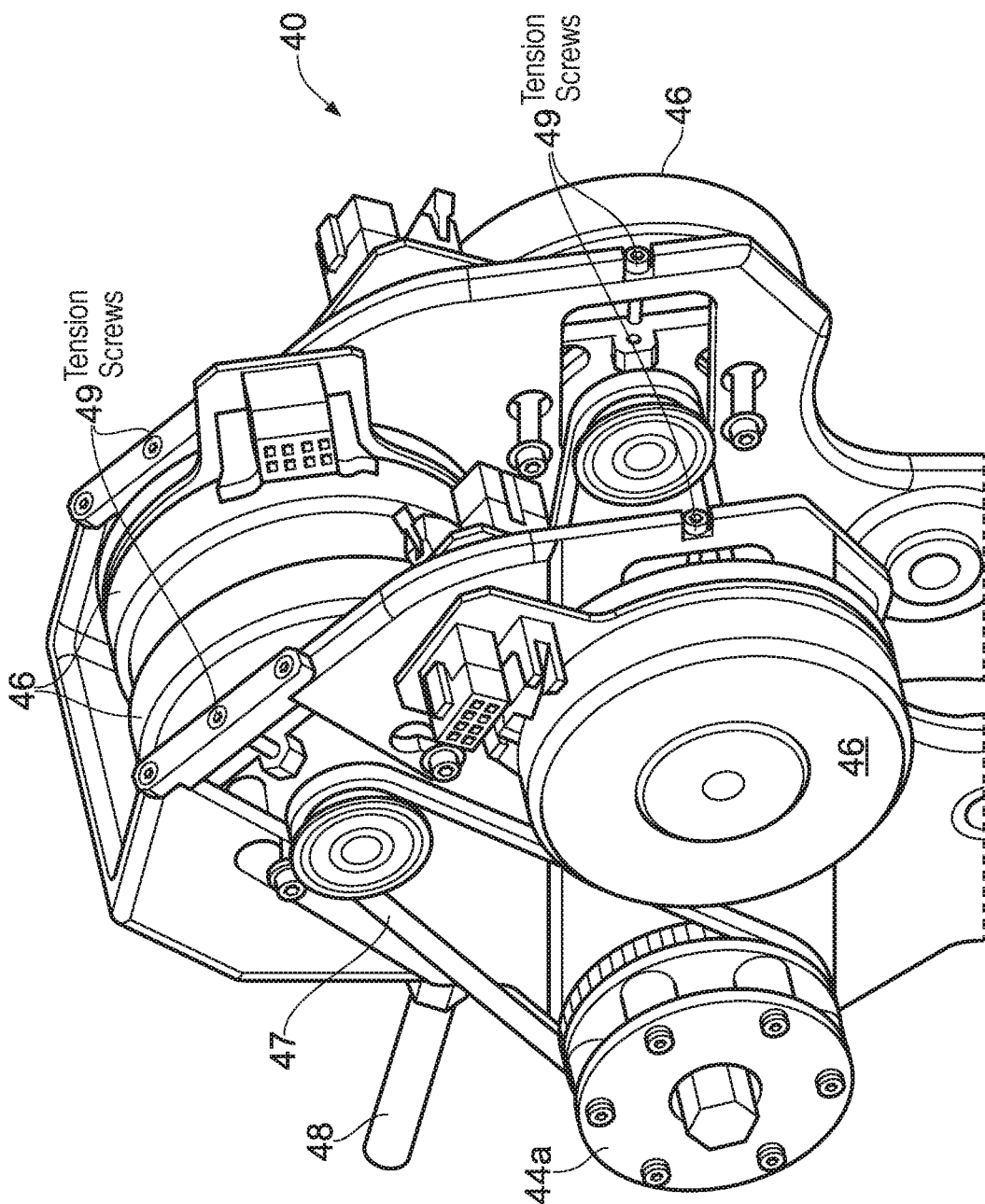

The pump assembly is shown in yet more detail in FIG. 8, where each of the four pump drive motors 46 are visible along with one of the toothed drive belts 47 and tension screws 49, used to impart tension in the drive belts 47. The drive belts' pulleys are sized to provide approximately a 2:1 reduction in speed of the motor at the pump head.

Figure 9:
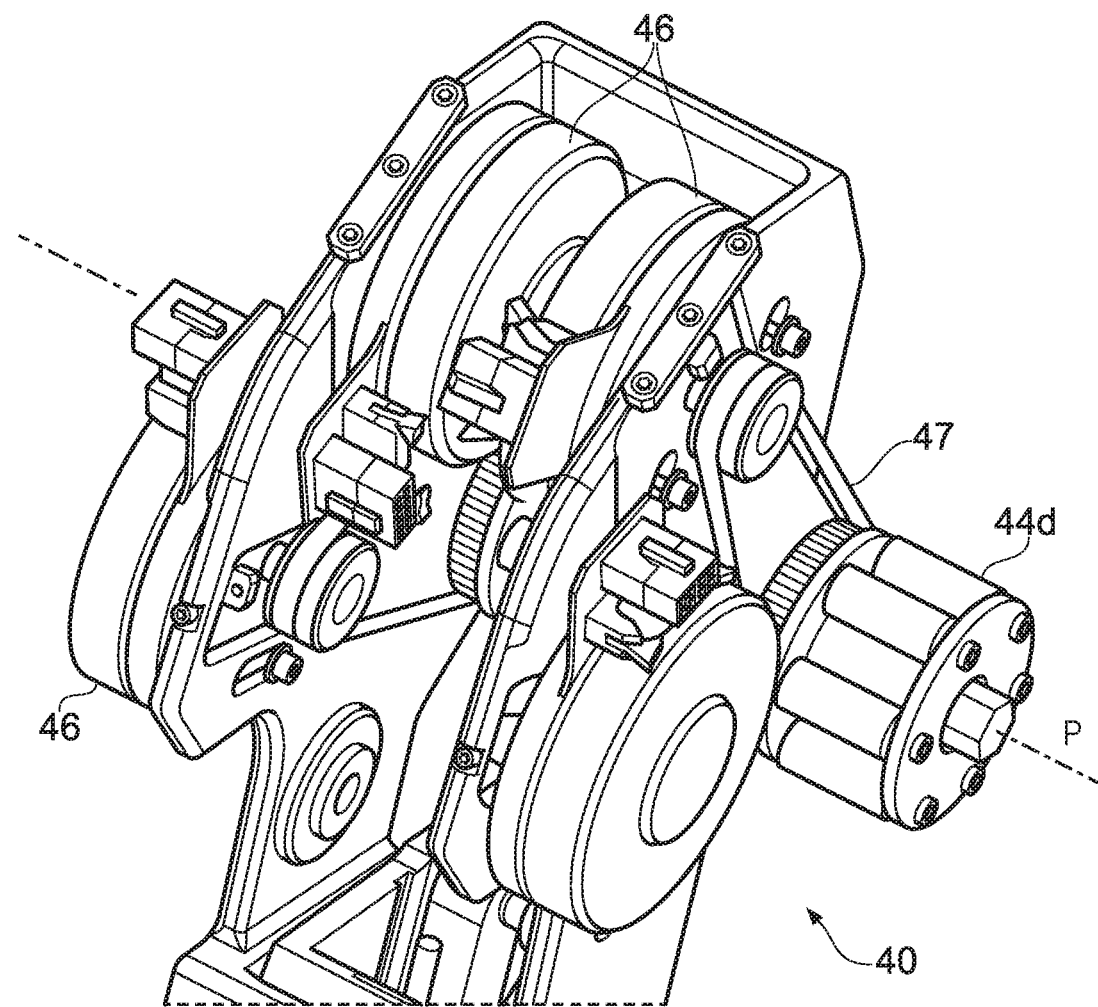

FIG. 9 shows another view of the pump assembly. In this view the pump head 44d is shown. It will be observed that this pump head is wider than the other pump heads in the pump axis direction P. This wider pump head 44d allows two or more flexible tubes to be engaged simultaneously, thereby providing increased fluid flow if required. This wider head arrangement allows a processing pump flow rate of up to 3000 mL/min at around 280 rpm motor speed.

Figure 10:
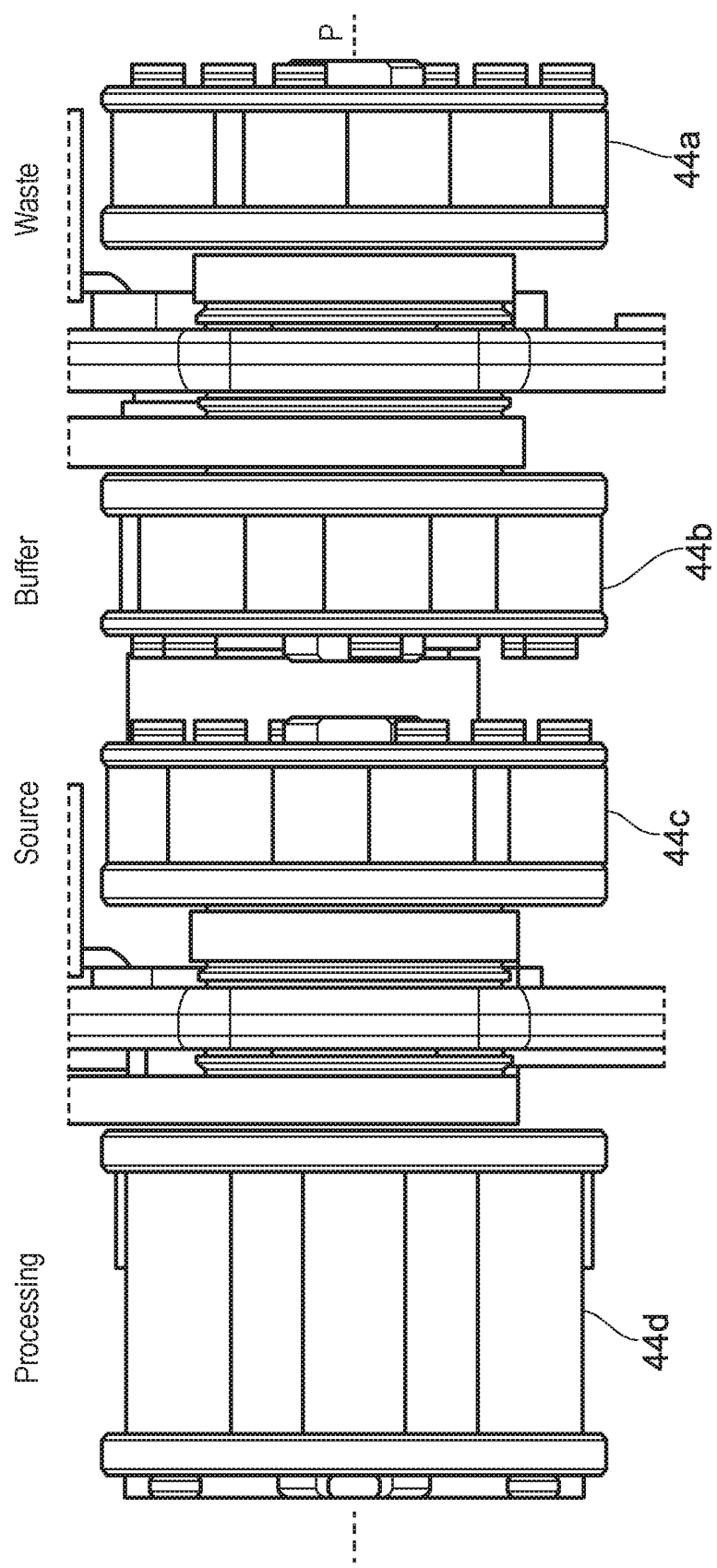

FIG. 10 shows the pumps heads 44a,b,c and d. As labelled, it can be seen that the four heads function to circulate fluid from the processing reservoir 150, to the filter 140, and back to the reservoir or to a collection point 127 (head 44d acting on tube 120d), to bring in cells in suspension from the source 125 (head 44c acting on tube 120c), to bring in buffer/wash solution 123 (head 44b acting on tube 120b) and to remove waste permeate 129 from the filter 130 (head 44a acting on tube 120a). As mentioned above, from speedier processing more than one tube 120 may be provide for each pump head, thus wider head 44d may in other arrangements act on more than one tube 120.

Figure 11:
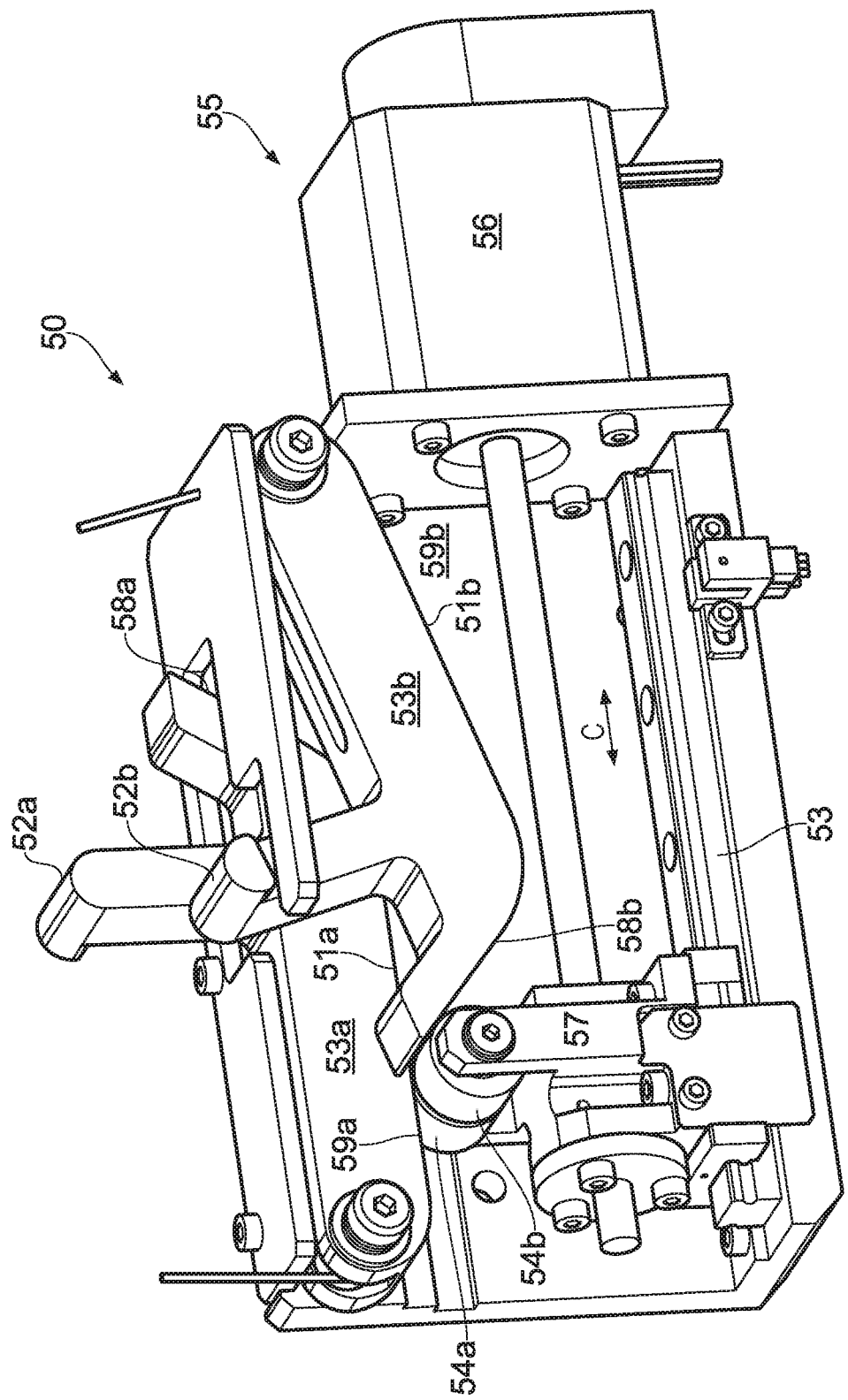
FIGS. 11 and 12 show details of a pinch valve again mountable to the frame shown in FIG. 5.

FIG. 11 shows a pinch valve assembly 50 which is mounted underneath the pump motor 464 and pump head 44 and pivots into position ready for operation together with the pump assembly 40. The pinch valve assembly 50 closes and opens process and collection fluid paths by pinching the tubes 130a and 130b against the anvil surface 32. The assembly includes a single linear actuator 55 which includes an electric stepper motor 56, for rotatably driving a lead screw 58 both clockwise and counterclockwise, which in turn moves a carriage 57 linearly back and forth in the direction of arrow C on a rail 53. The carriage 57 includes two rollers 54a and 54b, which act on cam profiles 51a and 51b formed on the back of two spring loaded valve arms 53a and 53b. The arms 53a and 53b are urged against the respective rollers 54a and 54b. The arms have fingers 52a and 52b, the tips of which press against the tubes 130a and 130b aligned in the valve's operative position with the anvil 32. The cam profiles 51a and 51b have 'open' portions (58a and 58b) which allow fluid flow and 'closed' portions (59a and 59b) which prevent substantial flow. Since the fingers are arranged in opposite orientations, the sequence of open and closed positions for the two fingers is: 130a closed, 130b open (the position shown in FIG. 11); 130a closed, 130b closed (at the mid-position of carriage 57); and 130a open, 130b closed (at the rightmost position of the carriage 57 when viewed in the same direction of view as illustrated in FIG. 11). It will be noted that no power is needed to hold the arms in the open or closed positions, because such positions may need to be maintained for long periods of time during possessing. It should also be noted that an open/open position is deliberately not possible to prevent unwanted fluid flows.

Figure 12:
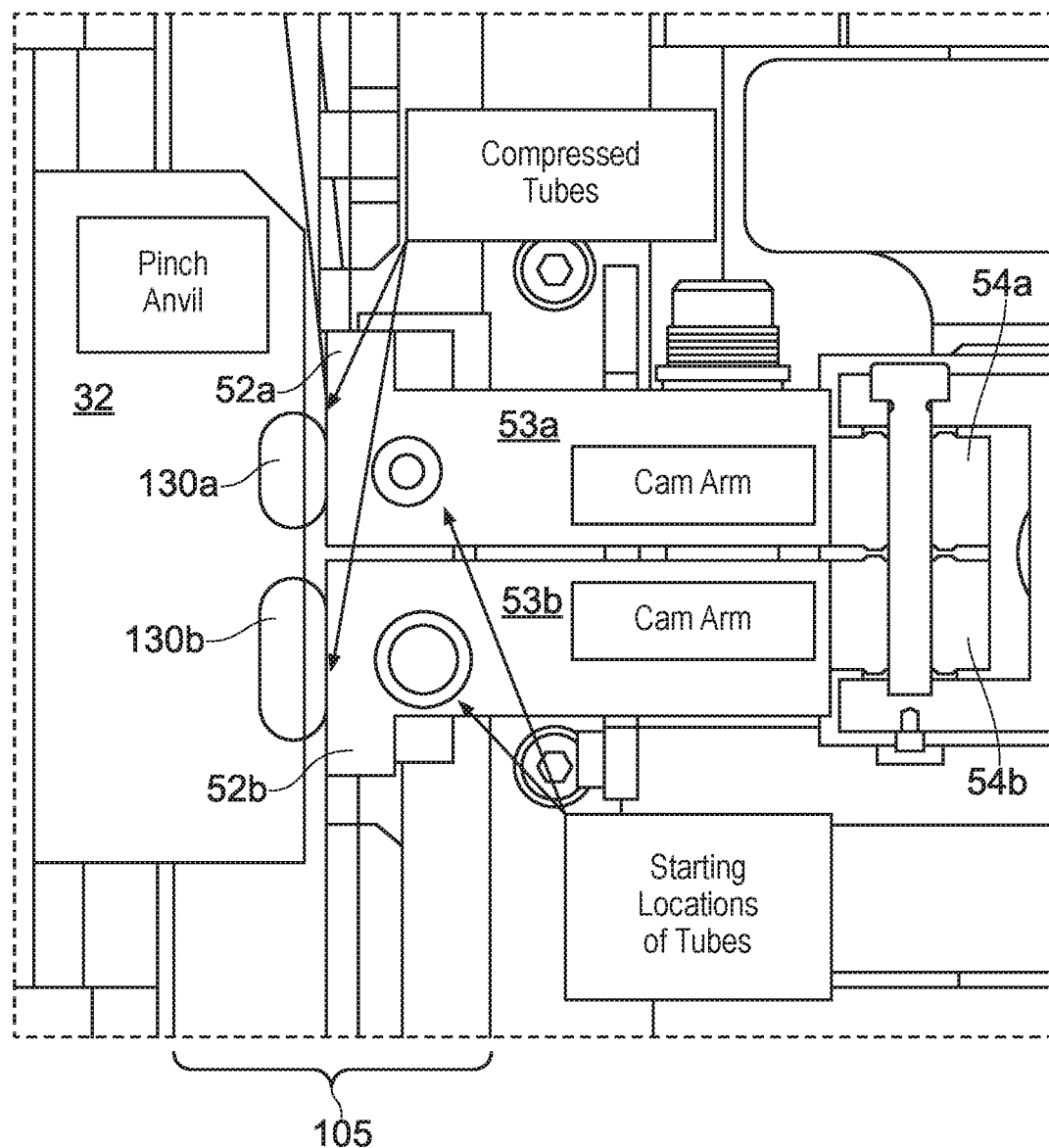

FIG. 12 shows a horizontal cross section through the anvil 32, through the valve arms 53a and 53b and through carriage rollers 54a and 54b, which in this view are in their mid-position, such that both fingers 52a and 52b are acting to compress and thereby close flexible tubes 130a and 130b (shown schematically in this illustration). It will be noted that the starting positions of the tubes is also illustrated. In order that the thickness of the processing kit frame 105 can be accommodated, the fingers 52a and 52b are initially retracted (along with the pump heads), and are only brought into a position ready to operate by pivoting forward of the pump assembly 40 once the processing kit 100 is in place. Then the fingers operate by opening or closing the tubes according to an operation protocol. The valve assembly 50 can be adjusted initially independently of the position of the pump assembly 40, so that the correct pinch load can be obtained.

Figure 13:
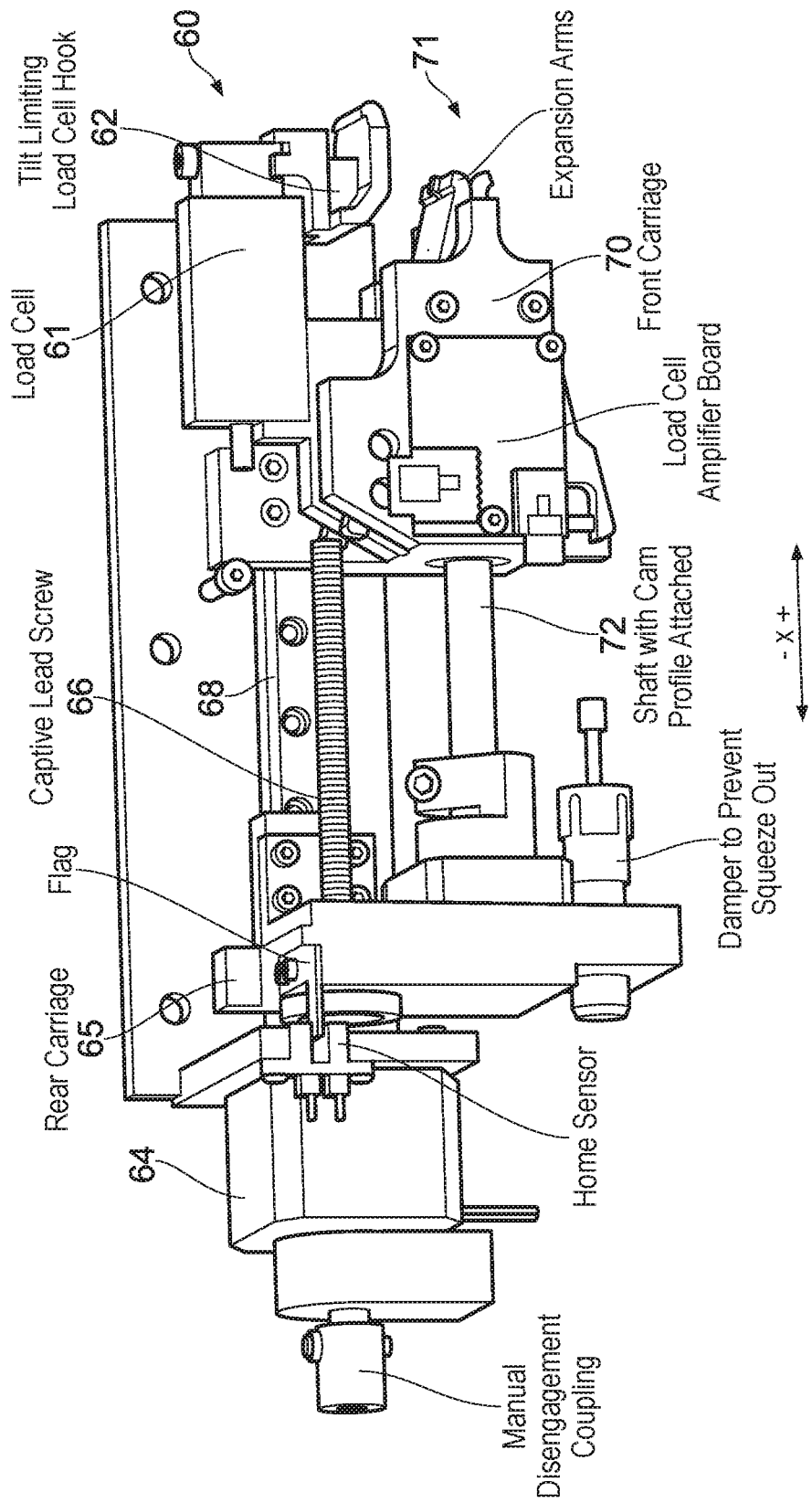
FIG. 13 shows a pictorial view of a processing reservoir transfer mechanism.

FIG. 13 shows a transfer mechanism 60 housed within the housing 12 for transferring the processing reservoir 150 of the processing kit 100 onto a weighing hook 62 so that the volume of liquids in the reservoir can be estimated in use. In practice the mechanism 60 removes the reservoir 150 from the processing kit support frame 105, transfers it to hook 62, which is supported by a load cell 61 where it will stay for the duration of a processing run, and then returns the reservoir 150 to the support frame 105. The processing reservoir 150 is mounted on the support frame 105 as supplied to the user and inserted into the housing in that state. It is reattached to the support frame before the user removes the processing kit from the housing. During a run, the process reservoir and connected tubing will hang freely on the load cell hook to enable mass measurement.

Figure 14:
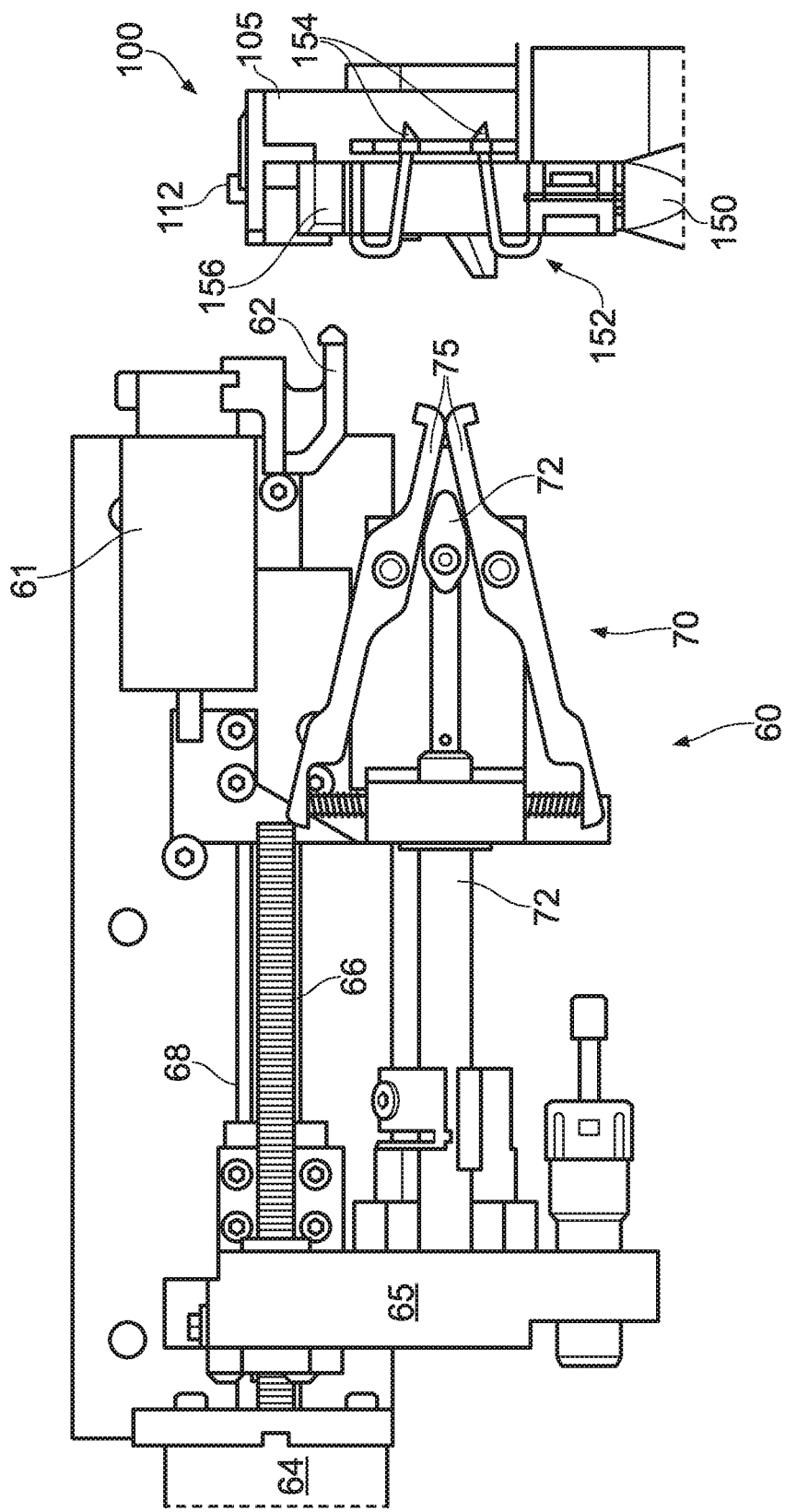
FIGS. 14 to 19 show side views of the transfer mechanism of FIG. 13, in different functional positions.

The motion of the mechanism 60 is controlled by one stepper motor 64 and a lead screw 66 which directly controls X direction movement of a rear carriage 65, travelling on a linear rail 68 as the lead screw 66 is rotated by the motor 64. The rear carriage 66 supports an extension shaft 73 that moves with the carriage 66. The shaft 73 has a distal end 71 which includes a profiled head 72 (FIG. 14). A front carriage 70 is moveable on the rail 68 also, but is not driven by the lead screw. Rather its movement is controlled by movement of the profiled head 74 and explained in more detail below.

The mechanism 60 starts in the position shown in FIG. 14, which is a side view in the direction of arrow y in FIG. 5. That position allows for insertion of the processing kit 100 into the housing 12, and brings the hanger 152 of the processing reservoir into an alignment with the mechanism 60. The hanger 152 includes two resilient arms 154 which sit in supporting apertures in the processing kit frame 105. In this initial position the hanger arms support the processing reservoir and keep it resiliently in place on the frame 105. On the hanger 152, above the arms is a further aperture 156 which accepts the hook 62.

Figure 15:
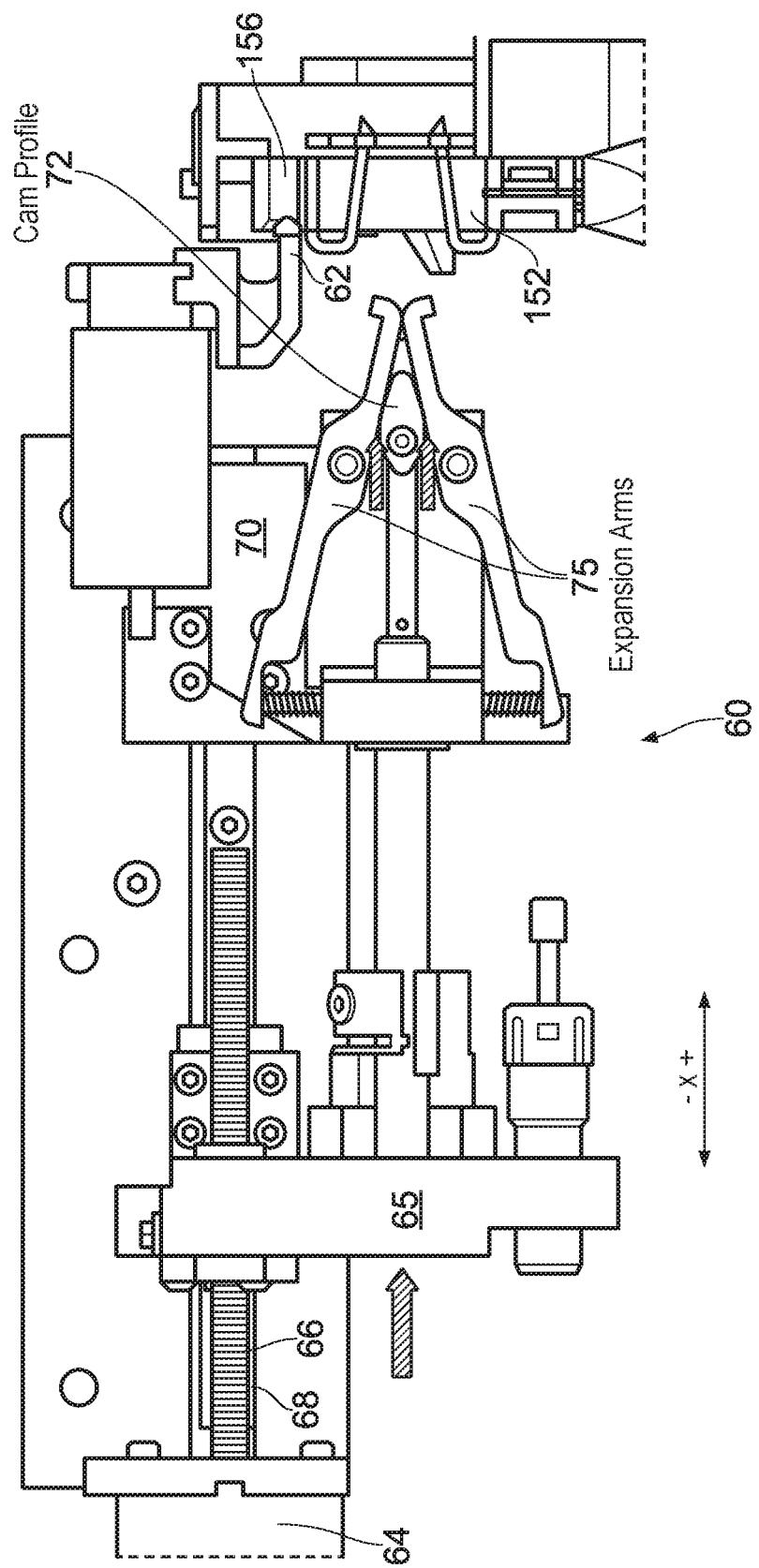
Figure 16:
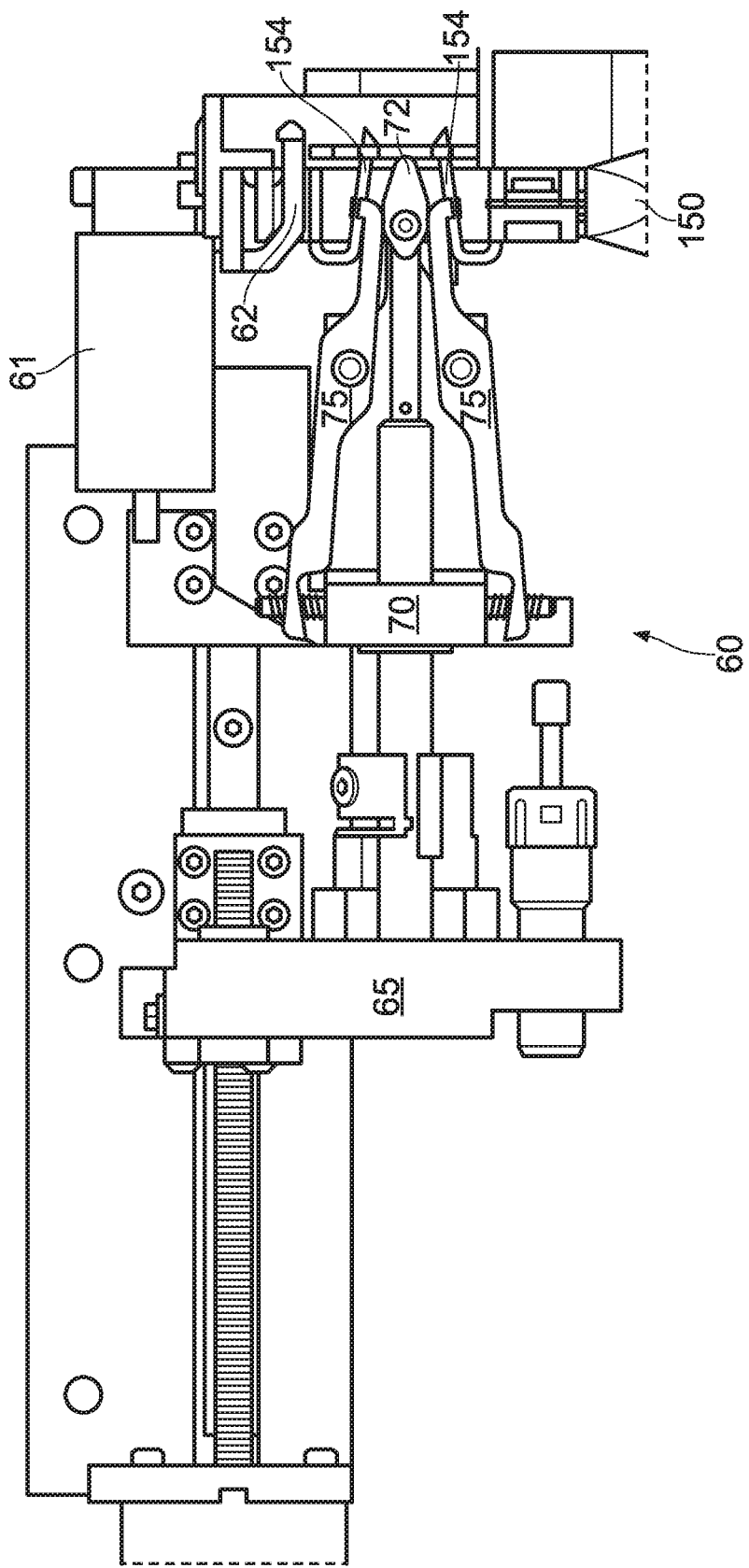

The rear carriage 65 is then driven in the positive X-direction as shown in FIG. 15. This movement ultimately pushes the profiled head 72 into a latch arrangement which has a pair of sprung expansion arms 75. The spring force required to open the expansion arms 75 is such that the expansion arms remain closed and the front carriage 70 is driven forward in the positive X direction also as shown in FIG. 15. The front carriage 70 is driven forward in this way until it reaches a hard stop formed by the reservoir clip on the support frame, as shown in FIG. 16. The frame 105 cannot move because it is being held in place by the upper and lower guides of the guide rails 22 and 24. Thus, the rear carriage continues to move forward while the front carriage is stopped, causing the profiled head 72 to force apart the expansion arms 75 apart and into latching cooperating engagement with the resilient arms 154 of the hanger 152. In this position the expansion arms distort the resilient arms to release their grip on the hanger 152, and the hook 62 enters the aperture 156.

Figure 17:
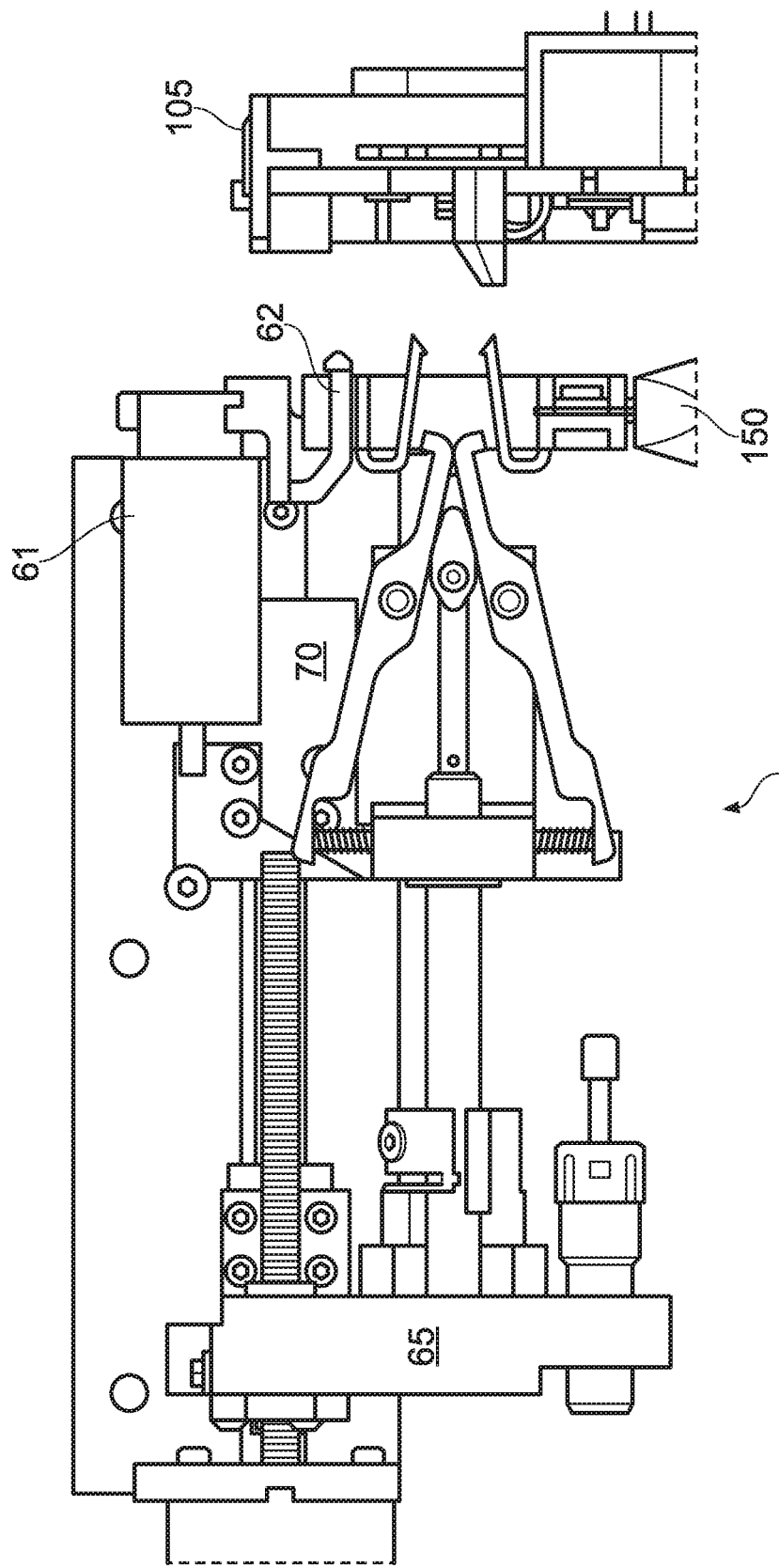

Next, as shown in FIG. 17, the rear carriage is driven by the motor 64 and leadscrew 68 in the negative X direction, thereby detaching the hanger 152 from the frame 105, and moving the hanger 152, with the reservoir 150 away from the frame 105.

The front carriage 70 is dragged backwards until it hits a stop. In this position the hanger 152 drops onto the load cell hook 62. The rear carriage 65 continues moving and the profiled head 72 is pulled out from between the expansion arms 75, thus returning them to their neutral position shown. At this point the hanger 152 is no longer held in place by the expansion arms and therefore slides down the load cell hook 62, finally bringing weight to bear on the load cell 61. The rear carriage 65 is now back to its initial, home position, and no parts of the mechanism, apart from the hook 61 touch the reservoir 150, or its hanger 152.

Figure 18:
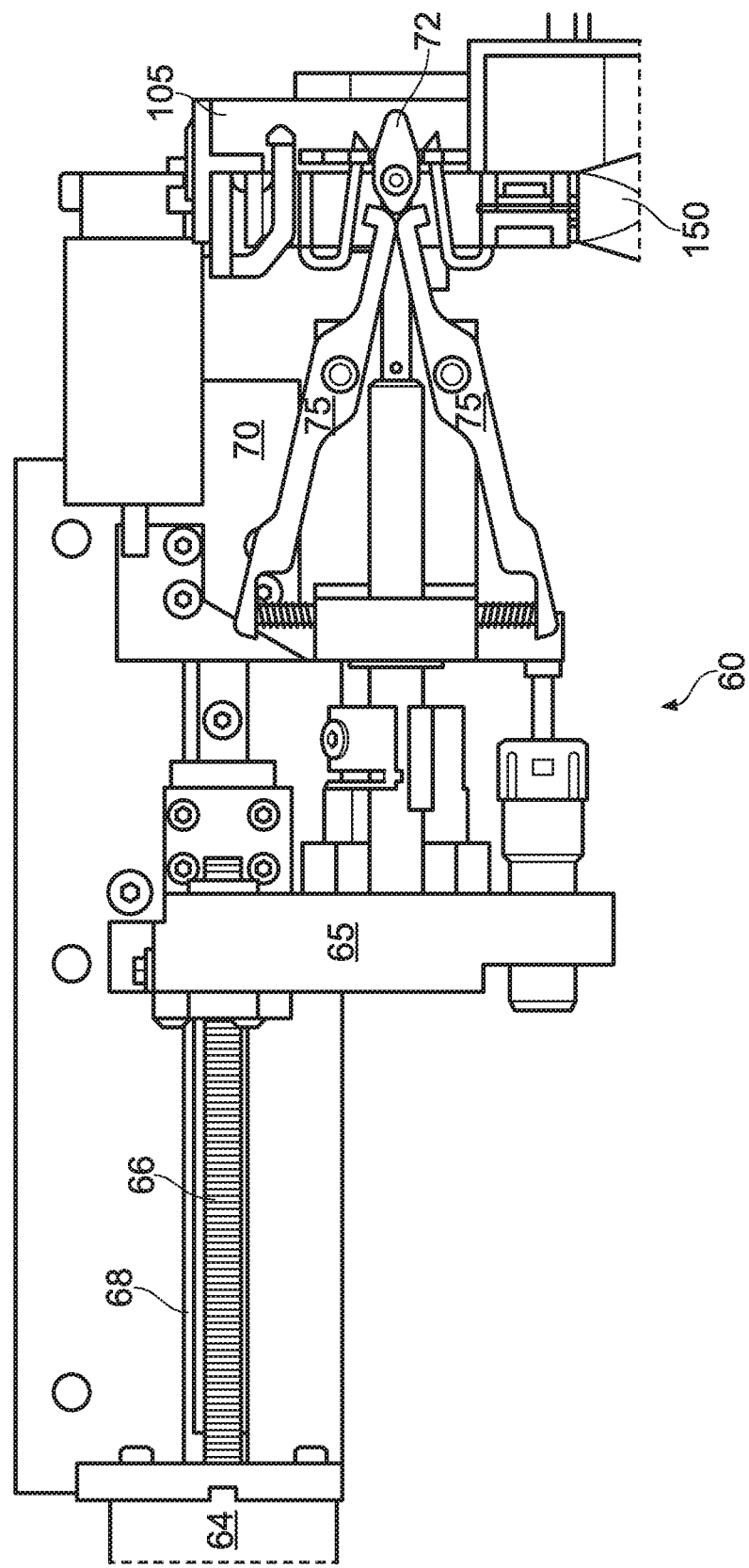

Returning the reservoir 150 to the frame 105 is carried out by reversing the steps described above. The front carriage 70 reaches a stop when the hanger 152 is flush against the support frame 105, with the support frame 105 held in place by the upper and lower guides 22 and 24. The rear carriage 65 continues to drive forward and pushes the expansion arms apart. This step ensures that the hanger 152 is properly located in the Z-dimension and that the resilient arms 154 are met with no resistance passing through their apertures on the frame 105. This action is different from the reservoir retrieval described above; the profiled head 72 is driven past the ends of the expansion arms 75, as shown in FIG. 18.

Figure 19:
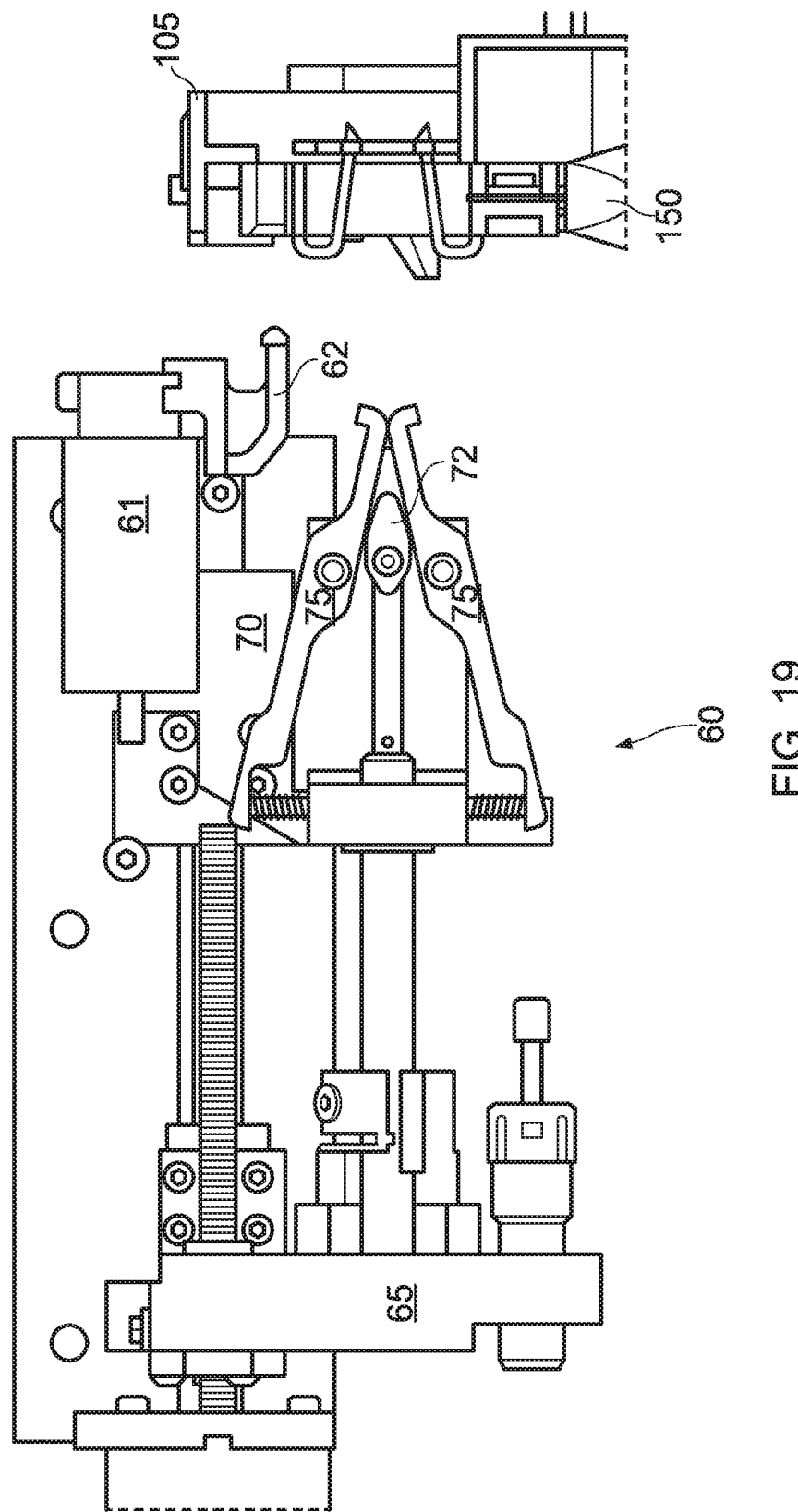

In this position, the hanger 152 will be securely reattached to the support frame 105 and the expansion arms 75, profiled head 72, and load cell hook 62 can be extracted. The rear carriage 65 drives backwards, dragging the front carriage 70 with it. The front carriage 70 reaches a stop while the rear carriage 65 continues moving backward. This allows the profiled head to be pulled through the expansion arms 75 once again and reset for a new process kit and new processing reservoir, as shown in FIG. 19.

In operation, the instrument 10 includes mechanical elements including the pump, pinch valve and weighing mechanisms described above, which are reusable, together with a removeable and disposable low cost processing kit 100 which comprises all the fluid elements (e.g. paths 110, filter 140 and fluid processing reservoir 150) necessary for cell harvesting. The combination of these features results in a cell harvesting instrument which is easy to use and can be readied for the next harvesting batch quickly. No mechanical parts come into contact with fluids, which means that cleaning of the mechanical parts between harvesting is not required. The instrument 10 is particularly suitable for concentrating and/or washing human cells, for example for subsequent use in cellular therapeutic applications where the readily achievable aseptic operating conditions of the instrument provide a much improved chance of therapeutic success, as well as reduced costs and turn-around times.

While only certain features of the invention have been illustrated and described herein, many modifications and changes will occur to those skilled in the art. It is, therefore, to be understood that the appended claims are intended to cover all such modifications and changes as fall within the scope of the invention. Further, it is intended that combinations of features contained in dependent claims are so combined for convenience, and any one or more of those combined features may be removed, replaced or moved into other claims without introducing new matter.

The invention claimed is:

1. A cell harvesting processing kit for at least one of separating cells from fluids and washing cells, the kit comprising:
   sealed fluid paths, at least a portion of which are formed from flexible tubing suitable for being externally manipulated by mechanical elements,
   a fluid processing reservoir and a filter suitable for retaining cells whilst permeating fluids in said paths,
   wherein the fluid paths are supported by a generally flat supporting frame such that said paths, reservoir and filter are arranged in a generally flat plane; and
   wherein said supporting frame includes through-apertures, and said flexible tubing is arranged to extend across said apertures such that the tubing is accessible from both sides of the flat supporting frame to allow said external manipulation from both sides of the frame.

2. The kit of claim 1, wherein said fluid processing reservoir is in the form of a container which lies generally flat in the frame and is demountable from the frame and re-attachable to the frame.

3. The kit of claim 1, wherein said fluid paths include at least one inlet located at the ends of extended flexible tubing for further fluid connection remote from the frame.

4. The kit of claim 3, wherein the plural fluid paths and extended fluid paths form a closed fluid processing system arranged such that fluids in the paths do not contact mechanical elements which effect fluid control.

5. The kit of claim 3, wherein said fluid paths further include at least one outlet.

6. The kit of claim 3, wherein the plural fluid paths and extended fluid paths form a closed fluid processing system arranged such that fluids in the paths do not contact at least one of a fluid pump or pumps and a fluid valve or valves.

* * * * *